(12) United States Patent
Zumbach et al.

(10) Patent No.: US 10,494,243 B2
(45) Date of Patent: Dec. 3, 2019

(54) ACTIVATING DEVICE FOR SCREW CAPS

(71) Applicant: CTC ANALYTICS AG, Zwingen (CH)

(72) Inventors: Melchior Zumbach, Lenzburg (CH); Roland Kernen, Muttenz (CH)

(73) Assignee: CTC ANALYTICS AG, Zwingen (CH)

( * ) Notice: Subject to any disclaimer, the term of this patent is extended or adjusted under 35 U.S.C. 154(b) by 555 days.

(21) Appl. No.: 14/577,714

(22) Filed: Dec. 19, 2014

(65) Prior Publication Data

US 2015/0175289 A1 Jun. 25, 2015

(30) Foreign Application Priority Data

Dec. 20, 2013 (EP) .................................... 13405141

(51) Int. Cl.
| | |
|---|---|
| *B67B 7/18* | (2006.01) |
| *B65B 7/28* | (2006.01) |
| *B67B 3/20* | (2006.01) |
| *B65B 69/00* | (2006.01) |
| *G01N 35/04* | (2006.01) |

(52) U.S. Cl.
CPC ............ *B67B 7/182* (2013.01); *B65B 7/2835* (2013.01); *B67B 3/20* (2013.01); *B65B 69/00* (2013.01); *G01N 2035/0405* (2013.01)

(58) Field of Classification Search
CPC .. G01N 2035/0405; B67B 7/18; B67B 7/182; B67B 3/2073; B67B 2201/10; B67B 3/20–2093; B67B 3/28; B65B 7/2835
USPC .................................... 53/492, 381.4; 81/3.2
See application file for complete search history.

(56) References Cited

U.S. PATENT DOCUMENTS

| | | | |
|---|---|---|---|
| 2,644,354 A * | 7/1953 | Schlageter | ................ B67B 7/18 |
| | | | 279/116 |
| 3,795,158 A | 3/1974 | Morita | |
| 4,222,214 A * | 9/1980 | Schultz | ................ B67B 3/2073 |
| | | | 279/33 |
| 4,696,144 A * | 9/1987 | Bankuty | ............... B67B 3/2053 |
| | | | 53/314 |
| 4,919,014 A | 4/1990 | Chen et al. | |
| 5,027,932 A * | 7/1991 | Graffin | .................. B23P 19/065 |
| | | | 192/150 |
| 5,148,652 A * | 9/1992 | Herzog | ................. B65B 7/2835 |
| | | | 451/451 |
| 5,345,844 A * | 9/1994 | Marsaw | .................. B67B 7/182 |
| | | | 81/3.2 |

(Continued)

FOREIGN PATENT DOCUMENTS

| | | |
|---|---|---|
| DE | 195 08 379 C1 | 7/1996 |
| EP | 0 736 481 B1 | 10/1999 |

(Continued)

*Primary Examiner* — Stephen F. Gerrity
*Assistant Examiner* — Joshua G Kotis
(74) *Attorney, Agent, or Firm* — Birch, Stewart, Kolasch & Birch, LLP

(57) ABSTRACT

A device for activating a screw cap of a container comprises a first holding device for holding the screw cap, and a drive for activating the first holding device, wherein the first holding device is movable in a plane. The first holding device comprises a coupling device for the coupling of an external drive, and therefore the first holding device is movable in the plane.

4 Claims, 5 Drawing Sheets

(56) References Cited

U.S. PATENT DOCUMENTS

| | | | |
|---|---|---|---|
| 5,417,031 A * | 5/1995 | Bankuty | B65B 7/2835 53/331.5 |
| 5,819,508 A | 10/1998 | Kraft et al. | |
| 6,125,718 A * | 10/2000 | Hill | B67B 7/182 81/3.2 |
| 6,158,196 A * | 12/2000 | Trebbi | B67B 3/2073 53/317 |
| 6,250,046 B1 * | 6/2001 | VandeGeijn | B23B 31/113 53/317 |
| 6,257,091 B1 * | 7/2001 | Cohen | B67B 7/182 81/3.2 |
| 7,383,753 B1 | 6/2008 | Hajianpour | |
| 7,398,714 B1 | 7/2008 | Mah et al. | |
| 7,972,579 B2 * | 7/2011 | Brunner | B01L 9/06 422/560 |
| 8,028,816 B1 | 10/2011 | Smith et al. | |
| 9,796,574 B2 * | 10/2017 | Frey | B23Q 3/15786 |
| 2001/0013169 A1 * | 8/2001 | Fassbind | B67B 7/182 29/773 |
| 2003/0061911 A1 * | 4/2003 | Niwayama | B67B 7/02 81/3.2 |
| 2003/0070510 A1 * | 4/2003 | Tremblav | B67B 7/182 81/3.2 |
| 2003/0196519 A1 * | 10/2003 | Graffin | B67B 3/26 81/3.2 |
| 2005/0028646 A1 * | 2/2005 | Hefti | B67B 7/18 81/3.4 |
| 2006/0032336 A1 * | 2/2006 | Wu | B67B 7/182 81/3.2 |
| 2007/0098597 A1 | 5/2007 | Brunner | |
| 2010/0281825 A1 * | 11/2010 | Corniani | B67B 3/2086 53/317 |
| 2011/0094616 A1 * | 4/2011 | Hayakawa | B67C 3/242 141/1 |
| 2011/0302883 A1 * | 12/2011 | Monti | B65B 3/003 53/281 |
| 2012/0311963 A1 * | 12/2012 | Fukuda | B67B 3/2053 53/317 |
| 2014/0311090 A1 * | 10/2014 | Weber | B67B 7/182 53/381.4 |
| 2017/0283231 A1 * | 10/2017 | Figa | B67B 7/18 |

FOREIGN PATENT DOCUMENTS

| | | |
|---|---|---|
| EP | 0 972 744 A2 | 1/2000 |
| EP | 1 705 149 A2 | 9/2006 |

\* cited by examiner

ACTIVATING DEVICE FOR SCREW CAPS

BACKGROUND OF THE INVENTION

Field of the Invention

The invention relates to a device for activating a screw cap of a container, comprising a first holding device for holding the screw cap, and a drive for activating the first holding device.

Description of Related Art

Devices for activating a screw cap of a container are widely known to a person skilled in the art and serve, for example, for handling samples in chemical analysis. With such devices for activating a screw cap, containers, such as vials or the like, can be screwed down with a screw cap or a screw cap can be removed.

EP 0 736 481 B1 (Roche) relates to a device for twisting off closures of sample vessels. For this purpose, the reagent vessels are clamped between holding jaws which are fastened to adjusting jaws in such a manner that they can be tilted in relation to the axis of the vessel. The adjusting jaws are movable via a spindle drive which is operated by an individual motor. A closure holding device is equipped with holding elements which have a plurality of gripping jaws. The gripping jaws can be moved by a drive with a pressure cylinder or a spindle drive. The closure holding device is located on a movement device which can both move the closure holding device parallel to the vessel axis and permits rotation of same about the vessel axis. This is achieved by a motor-driven screw and a nut. The nut can be locked with a pin in such a manner that the vessel can be rotated.

The device comprises a left and a right tripod leg and a transport belt in between for the sample vessels. A gripper with gripping jaws for removing vessels from a rack is movable vertically via a spindle, and therefore a closure can be guided over a vessel held by the holding jaws. The closure holding device which is driven by a motor with toothed belts comprises a nut with depressions into which a push rod can be introduced for securing against rotation. The push rod is activated via a lifting magnet.

For the vessel holding device, use is made of a dedicated motor which transmits the rotational movement thereof via a toothed belt to the two vessel holding jaws. After removal, the closures can be dropped into a catching device moving under the closure.

EP 0 972 744 A2 (Bayer) relates to an automatic decapper for opening various closures, in particular rotary and plug-in closures of test tubes of differing sizes for use in analyzers. The device comprises upper grippers which hold the cap in a fixed position, and lower grippers and also means for rotating and translating the lower grippers away from the upper gripper. The upper gripper can be mounted on a pivotable arm and comprises a jaw chuck. The lower gripper comprises a screw for the height adjustment of the gripping device. The drive takes place by means of a motor and via a toothed belt drive. The lower gripper comprises two spring-loaded holding arms which are activatable by motor.

The known devices for activating screw caps have the disadvantage of being of complex construction and therefore expensive to produce.

SUMMARY OF THE INVENTION

It is the object of the invention to provide a device for activating screw caps, which device belongs to the technical fields mentioned at the beginning and can be produced cost-effectively.

According to the invention, the first holding device comprises a coupling device for the coupling of an external drive, and therefore the first holding device is movable by means of the external drive.

Owing to the fact that the device does not require a dedicated drive for moving the first holding device, the device can be constructed particularly simply. It therefore suffices if the first holding device is designed to be movable, for example, via linear guides or the like. According to the invention, the device therefore does not comprise a dedicated drive for moving the first holding device.

The external drive is preferably incorporated by a secondary device which already has the required equipment for moving the holding device. Such a secondary device can be designed, for example, as a robot for container transport. The robot can therefore be designed in such a manner that containers can additionally also be grasped and transported. This is of particular advantage since typically a transport device for the containers for transporting the containers from a rack or the like to the device and back is in any case provided.

Furthermore, a robot which moves a syringe or an SPME device can also be used as the external drive, that is to say, a robot which, in addition to the device-specific movement steps, can also take on further functions. The robot can therefore be designed in such a manner that a plurality of functions can be taken on together. Existing resources can therefore be better utilized, and therefore the device according to the invention can be constructed particularly cost-effectively and simply. See in this respect further below with regard to the arrangement comprising a device and an external drive.

The first holding device is preferably movable in a plane. The plane is preferably a plane which is parallel to an axis of rotation of a container, in particular a vertical plane. It is therefore made possible that, with the device, a container can be grasped at the screw cap via the movable holding device if said container is in said plane. A robot which transfers the container from a storage station, for example a rack, into said plane can be provided in the process. Owing to the fact that the first holding device is movable in the plane, the space above the container can be released, for example, for a transport device, and therefore a container can be positioned from above in the plane in such a manner that the first holding device can subsequently be moved over the container and the cap can be grasped.

In variants, the holding device can also be movable merely in a z direction, and therefore it is possible merely to take a container height into consideration.

The first holding device is preferably movable along a first axis and is pivotable about a second axis. The two movements, that is to say, both the moving and the pivoting, can in principle take place in the same plane, wherein, in this case, the plane is preferably oriented vertically or parallel to a container axis. So that the container can be positioned, for example by a transport apparatus, the first holding device can be pivoted out of the transport path, for example about a horizontal axis. The container can then be positioned, whereupon the first holding device is pivoted in again such that a cap receiver of the first holding device is oriented coaxially with respect to the screw cap of the container. In order to grasp the screw cap, the first holding device can subsequently be moved in the direction of the screw cap.

However, the first axis is particularly preferably oriented perpendicularly to the second axis. For example, the first axis can be oriented vertically such that the height of the first holding device can therefore be adjusted. In this case, the first holding device can be designed to be pivotable about a vertical axis, and therefore a three-dimensional movement of the first holding device is possible. The first holding device can therefore be moved in the form of a combined movement along a region of a cylinder jacket. In contrast to the above-described embodiment, the first holding device is pivoted out laterally, that is to say, in a plane perpendicular to the container axis, for the positioning of the container. After the positioning of the container, the first holding device is pivoted in again, and therefore a cap receiver of the first holding device is oriented coaxially with respect to the screw cap of the container. In order to grasp the screw cap, the first holding device can subsequently be moved in the direction of the screw cap.

The pivot axis has the advantage that it can generally be produced more cost-effectively than a linear guide. The overall costs of the device can therefore be reduced further.

In variants, two linear guides at right angles to each other can be provided, and therefore the first holding device can be moved in a plane spanned therewith. Furthermore, the first holding device can also be designed in such a manner that a three-dimensional movement is possible.

The device preferably comprises a second holding device for grasping the container. During the activation of the screw cap, the container is particularly preferably held by the second holding device. The container can therefore be held during the activation of the rotary closure, and therefore the rotary closure or screw cap can also be acted upon with a relatively large torque—this is of advantage both for opening and for closing the rotary closure. The second holding device can be formed in very different ways. Given a suitable shape of flask, a positive connection can be provided. However, the container is preferably grasped by means of a non-positive connection. This has the advantage that the second holding device can be designed in such a manner that it functions independently of the shape of flask. In a particularly preferred embodiment, a container is clamped by the second holding device in order to prevent rotation of the container during the activation of the screw cap. The second holding device is therefore designed as an actively activatable holding device.

Alternatively, the second holding device can also be dispensed with, with passive means being provided for holding the container. Said passive means can be provided, for example, in the form of a rest with a high frictional resistance, for example in the form of a rubber mat. Furthermore, said rest can also include a conical opening which is provided on the inner walls with a layer of increased stiction. The cone can be designed in such a manner that various container sizes can be picked up; for this purpose, said cone can also comprise individual frustoconical sections which are put together or arranged next to one another to form a stepped funnel.

The first and/or the second holding device are preferably designed as jaw chucks, and in particular for picking up screw caps or containers of differing diameter. A structurally simple and cost-effective first or second holding device is therefore achieved. In particular, containers or screw caps of differing diameters can be grasped in a simple manner with jaw chucks. The z-axis movability therefore produces a device for activating screw caps, which device is usable in a particularly versatile manner, since not only the diameters, but also the heights of the containers can vary. The containers can be present, for example, as vials and can hold volumes of from 2 ml to 40 ml. Of course, smaller containers with a capacity of less than 2 ml or larger containers with a capacity of more than 40 ml can also be provided. This depends on the dimensioning of the jaw chucks and the maximum movement distance of the first holding device in the z direction.

In a particularly preferred embodiment, one jaw chuck or the two jaw chucks is or are a three jaw chuck or a four jaw chuck.

A person skilled in the art knows variants to the jaw chucks, such as, for example, vice-grip wrenches or the like. In particular, the jaw chuck can also be designed as a two jaw chuck or as a jaw chuck with more than four jaws.

The first and/or the second holding device is preferably self-locking. The control of the device is therefore simplified since, after the grasping of the screw cap or of the container, the holding force does not have to be monitored further. In particular, a holding force can therefore be set precisely. This may be relevant in particular in the case of fragile containers, for example in the case of thin-walled glass vials, but also in the case of unstable screw caps. Furthermore, after the screw cap is grasped, the drive provided for grasping the screw cap can therefore be provided for one or more other uses, in particular for rotating the first holding device and therefore for screwing the cap on or down. The device can therefore be further simplified (see further below).

The two holding devices or one of the two holding devices can also not be designed to be self-locking. In this case, a separate locking device can be provided for the holding device.

The second holding device preferably comprises a central opening through which a container and/or screw cap held by the second holding device can be dropped. A catching vessel in which the containers which have been dropped are caught can be provided below said central opening. This design is advantageous in particular if it can be detected by the device that a container is defective. This situation may be present, for example, if a rotary closure is jammed, and this can be detected, for example, by the drive exceeding a torque limit. In this case, the container can simply be dropped through the opening in the second holding device, and therefore an efficient movement is possible if rejects are present.

In variants, the central opening can also be dispensed with. In this case, defective containers would be guided away, for example, by a robot.

An arrangement preferably comprises a device for activating a screw cap of a container, with a first holding device for holding the screw cap, and with a drive for activating the first holding device, wherein the first holding device comprises a coupling device for the coupling of an external drive, and therefore the first holding device is movable by means of the external drive. Furthermore, the arrangement comprises an external drive, in particular a robot for moving the first jaw chuck.

In a method for activating a screw cap of a container using an above-described arrangement, a first holding device is moved by an external drive, in particular a robot, and then the screw cap is grasped and activated by the first holding device.

In this combination, the device can be equipped with precisely one drive for the rotation and the activation of the holding device, and therefore a particularly cost-effective device is achieved (see below). In particular, a device-dedicated drive for moving the holding device can therefore be dispensed with. The robot can be provided specifically for moving the holding device. However, the robot preferably includes further tasks, such as, for example, the removing of samples from a container, for example via a syringe or an SPME device, etc. The device preferably comprises a horizontal and a vertical linear guide, and therefore the holding device is movable in the plane.

The external drive, in particular the robot, preferably comprises a coupling element, in particular a gripping element for grasping and moving the first holding device in the plane.

The coupling device can be designed in a wide variety of ways. Since the holding device in a first embodiment is movable merely in a plane, it suffices, for example, if the holding device is connected to an opening which is oriented at right angles to the plane and in which a correspondingly shaped counterpart of the external drive can engage. In this case, a coupling takes place in a particularly simple manner by the external drive being moved in such a manner that the counterpart enters the opening in the holding device. The holding device can subsequently be moved in the plane by the external drive. An opening here can be designed, for example, as a bore and the counterpart as a cylinder, or the opening can be designed as a slot and the counterpart as a plate. A person skilled in the art also knows further forms for the opening and the counterpart. In particular, the external drive can also include the opening and the holding device can also include the counterpart. It is furthermore also clear to a person skilled in the art that it is not absolutely necessary for the holding device itself to include the opening or the counterpart and instead another element which is movable together with the holding device and is therefore connected thereto can include such an opening or the counterpart.

In principle, the first holding device can also be movable three-dimensionally by the external drive. In particular, as described above, the first holding device can be movable along a region of a cylinder jacket. In such an embodiment, a positive-locking coupling can be provided for connecting the external drive to the first holding device. For this purpose, the coupling device can comprise, for example, a bayonet closure, but this coupling has the disadvantage that an activation of the coupling device is required, namely a rotation of one of the two cylindrical parts after same have been clamped together. However, the three-dimensional movement can also be achieved without activating the coupling device if the holding device takes up an inoperative position in a lowered state by means of gravity. In this case, the external drive can comprise, for example, an L-shaped element which can be introduced from below into a corresponding L-shaped opening. The first holding device can also be connected to a downwardly projecting pin which can be received in a correspondingly dimensioned sleeve which is connected to a robot. A person skilled in the art also knows further possibilities.

Alternatively, the device itself can comprise a drive for moving the holding device. As already mentioned, the holding device can be movable along a single axis (x, y or z axis) or else three-dimensionally both by an external and by an internal drive. The device can also be movable rotatably or pivotably. The external drive can also be connectable in a non-positive-locking manner to the first holding device, for example by a clamping device or the like.

In a further embodiment, the first holding device can comprise a central opening via which a screw cap, container or a container provided with a screw cap can be introduced. For example, an open container or an open vial can therefore be efficiently provided with a screw cap. In particular, for the screwing down with a screw cap, the container does not already have to be provided with a screw cap on insertion into the device, and therefore the screwing process can be carried out more efficiently and robustly. In order to further optimize the process, a stock of screw caps can be provided via the central opening in the first holding device, for example in a suitable tube or the like, wherein, for example, after the last screw cap has been screwed down, the holding device is raised by a cap height in order, with the holding device, to fixedly grasp the next screw cap which has slid down because of gravity. The holding device can subsequently be guided upward without available caps dropping out of the tube.

In variants, the central opening in the first holding device can also be omitted.

The external drive, in particular the robot, preferably comprises a picking-up device for picking up a container. The robot can therefore also be used, in addition to moving the first holding device, to position a container in advance in the second holding device. The resources are therefore optimally used in order to achieve as cost-effective an arrangement as possible with as few driving motors as possible.

In variants, this function of the robot can also be dispensed with.

The picking-up device preferably comprises a magnet for picking up the container. A structurally particularly simple picking-up device is therefore provided. The magnet can be designed, for example, as a permanent magnet, and therefore the picking-up device is further simplified. Also, the operation of the picking-up device can therefore be kept simple since the container is grasped as soon as the picking-up device is sufficiently close to the container. In order to set the container down, the latter can be inserted into a holding device, for example into the second holding device, whereupon the magnet can be removed, for example by a lateral movement of the magnet, for example in a direction at right angles to the introducing direction of the container, or by the holding device grasping the container such that the magnet can also be decoupled upward, counter to the introducing direction of the container.

The use of an electrically controllable magnet can be of advantage in order to be able to deposit the container in any position, in particular also on a flat surface. Furthermore, an electromagnet has the advantage that an inadvertent picking up of a container or of another metallic object in the periphery of the picking-up device, such as, for example, a paperclip or the like, can be avoided.

So that a container can be grasped with the picking-up device comprising a magnet, the container has at least one magnetic region. The latter can be present, for example, as a ferromagnetic cap. Furthermore, a cap can also be substantially produced from non-ferromagnetic material which, however, has ferromagnetic inclusions, for example a plastic with ferromagnetic metal splinter inclusions. In principle, the container can also have such inclusions. The container can also be equipped with a magnetic coupling part, for example a magnetic metal part on the container. For example, a label can also comprise a ferromagnetic metal part. Further possible embodiments of a container or a container cap, which can be grasped with a magnet, are also known to a person skilled in the art.

In variants, the picking-up device can also comprise a gripper, designed in the form of a gripper with two or more gripping arms or a jaw chuck. Finally, the first holding device can also be designed in such a manner that a container can be grasped and transported therewith. A very wide variety of suitable embodiments for this purpose are known to a person skilled in the art.

In a second aspect of the invention, a device for activating a screw cap of a container, in particular a container for use in a chemical analyzer, comprises a first holding device for holding the screw cap, and a drive for activating the first holding device, wherein the first holding device is settable into a rotational movement by the drive.

It is therefore possible, with a single drive, to activate the first holding device and also to set the first holding device into a rotational movement, and therefore a second, additional drive for one of the two functions can be dispensed with. Since the drives in such apparatuses generally contribute substantially to the overall costs of production, a particularly cost-effective device for activating a screw cap can therefore be achieved, and in particular, in conjunction with the external drive for moving the first holding device, the device can therefore be further simplified and produced more cost-effectively. The device is therefore additionally particularly robust during operation and needs little maintenance. Furthermore, the device can optionally also be designed to be more compact since only one drive has to be accommodated.

In a method for activating a screw cap of a container, a screw cap is grasped by the first holding device, by activation of the drive, and then the first holding device is set into a rotational movement by means of the same drive.

The first holding device is preferably moved because of the thread pitch of the screw cap or of the container in the direction of an axis of rotation of the first jaw chuck, which axis of rotation is defined by the rotational movement of the first holding device. This design is particularly advantageous since the device can be constructed particularly cost-effectively and simply and, in addition, a method for closing or opening a rotary closure is simple to control. This is particularly since no additional drive for compensating for a thread pitch has to be provided. Furthermore, no adaptation has to be undertaken when the container is changed, and therefore the device can be used particularly flexibly with regard to the container sizes. The compensation distance can be achieved, for example, by resiliently supporting the container. Preferably, however, the holding device is mounted displaceably in the z direction (in the direction of the axis of rotation) (see below). In the latter case, the weight of the holding device can be used as contact pressure force, and therefore the internal thread of the screw cap can optimally engage in the external thread of the container. The weight can also be adapted by standard means in the art, for example by springs, counterweights, lever systems, etc.

In variants, an additional drive which adapts the position of the first holding device with respect to the container to the current closed state of the screw cap can be provided.

The device preferably comprises a switchover device for switching over the device between a first configuration for activating the first holding device and a second configuration for setting the first holding device into a rotational movement. A separate activation of the two configurations can therefore be achieved, and therefore, in turn, for example, an activating force of the first holding device, in particular the holding force, can be activated independently of torque for the rotational movement. This design is particularly advantageous if, for example, a cap which is to be screwed onto the container is deformable, and the holding force of the holding device can thus be adapted to the stability of the screw cap. In such cases, for example before the screw cap is opened, the holding device can be activated with a greater force in order to overcome the stiction so that the holding device does not slip during the rotation of the screw cap. As soon as the screw cap is set into a rotational movement, the holding force can be reduced so that the screw cap is not crushed.

In variants or in addition, the device can also be constructed in such a manner that the two functions can be executed in parallel. For this purpose, a dedicated clutch can be provided for the two configurations, wherein the first holding device can be activated by the first clutch via the drive and the first holding device can be set into a rotational movement by the second clutch via the same drive.

The holding device is preferably designed as a self-locking holding device. For this purpose, the holding device can comprise, for example, holding jaws with a substantially tangential toothing, which holding jaws are movable radially by an axially rotatable, disk-shaped worm thread. The thread pitch here is preferably selected in such a manner that the self-locking can be achieved.

In variants, the holding device can also be designed in another manner, for example analogously to a drill chuck of a drill. Further possible holding devices are also known to a person skilled in the art.

The device preferably comprises an activating element which is rotatable about an axis of rotation of the holding device for activating the holding device, wherein rotation of the activating element is blockable by the switchover device such that the holding device is activatable by the drive. The holding device therefore preferably comprises a first region for holding the container cap and a second region which is designed as an activating element for the holding device. The first and the second region are preferably arranged coaxially, that is to say the two regions are preferably rotatable about the same axis. The holding device is preferably activated by means of a relative rotation between the holding device and the activating element.

In the method, the rotary closure of the container can then be grasped by the relative rotation between the holding device and the activating element. Both the holding device and the activating element are preferably subsequently set into a rotational movement, and therefore the rotary closure can be rotated.

The relative rotation between the holding device and the activating element is a rotation of one of the two elements (holding device and activating element) about the common axis of rotation about which the holding device and the activating element are rotatable.

Relative rotation is understood here as meaning that at least one of the two elements executes a rotational movement about said axis of rotation, wherein, however, the two elements do not execute the same rotational movement. It would in principle be conceivable for the activation of the holding device to be able to be achieved by the two elements rotating in the same direction or in an opposed direction to each other at different angular speed. However, in a preferred embodiment, the activation of the holding device is achieved by one of the two elements being blocked with respect to a rotation, and therefore only one of the two elements is set into a rotational movement.

In a particularly preferred embodiment, the activating element is designed as a disk with a helical thread while the holding device comprises holding jaws for holding a screw cap. However, it is clear to a person skilled in the art that the activating element and the holding device can also be designed in a different manner, for example in the form of a drill chuck or the like.

Additionally or alternatively, the switchover device can also block a rotation of the holding device. An additional blocking of the rotation of the holding device can be of advantage in particular if the holding device is not of self-locking design.

The switchover device preferably comprises a magnetically activatable bolt for blocking the rotation of the activating element. A particularly simple blocking device is therefore provided for the activating element which, in addition, is cost-effective to produce and robust in operation. In addition, this design of the blocking device is extremely simple to bring about—the activating element which is mounted rotatably about the axis of rotation merely has to be provided with a notch or depression for the bolt. In this case, the position of the notch or of the depression can be localized, for example with a sensor, in particular with a Hall sensor, and therefore the bolt can be activated precisely when the notch or depression is in a position in which the bolt can be driven into the notch or depression and can thus block the activating element. Instead of a notch, the activating element can also peripherally comprise a plurality of notches, in particular the activating element can comprise, for example, a toothed wheel mounted coaxially with respect to the axis of rotation, wherein the bolt can engage between two adjacent teeth in order to block the activating element.

In variants, the blocking device can also comprise a clamping device for the activating element, which latter can be prevented from rotating by means of a clamping operation. Other possibilities are also known to a person skilled in the art.

The drive is preferably designed as a belt drive, particularly preferably as a toothed belt drive.

The torque for activating and rotating the holding device is preferably transmitted here from the driving motor via a drive shaft with a drive wheel via the belt to the holding device. A cost-effective drive needing little maintenance is therefore achieved. The use of a belt or toothed belt has the advantage that large impulses, for example when starting up, can be absorbed by the, even if slight, extensibility of the belt. Furthermore, the drive can be designed in such a manner that, at too large a torque, the belt slips at the drive wheel, and therefore damage to the device can be avoided. Said slip clutch can also be dispensed with, in particular if the motor is controllable via the torque. In particular in the latter case, the belt drive is preferably designed as a toothed belt drive. This has the advantage that it does not have any slip. This is important, for example, in the case of position regulations, if the transducer is flange-mounted on the motor. Finally, a greater torque can be transmitted with a toothed belt drive than is possible in the case of a comparable belt drive which is subject to stiction.

In variants, a drive can also be provided via a drive chain, or a direct drive can be provided via a gearing or toothed wheels.

The container and/or the screw cap, in particular in the event of identification of a reject, is dropped through a central opening in the second holding device.

Further advantageous embodiments and combinations of features of the invention emerge from the detailed description below and the entirety of the patent claims.

BRIEF DESCRIPTION OF THE DRAWINGS

In the drawings used for explaining the exemplary embodiment.

Identical parts are basically provided with the same reference numbers in the figures.

DETAILED DESCRIPTION OF THE INVENTION

Figure 1:
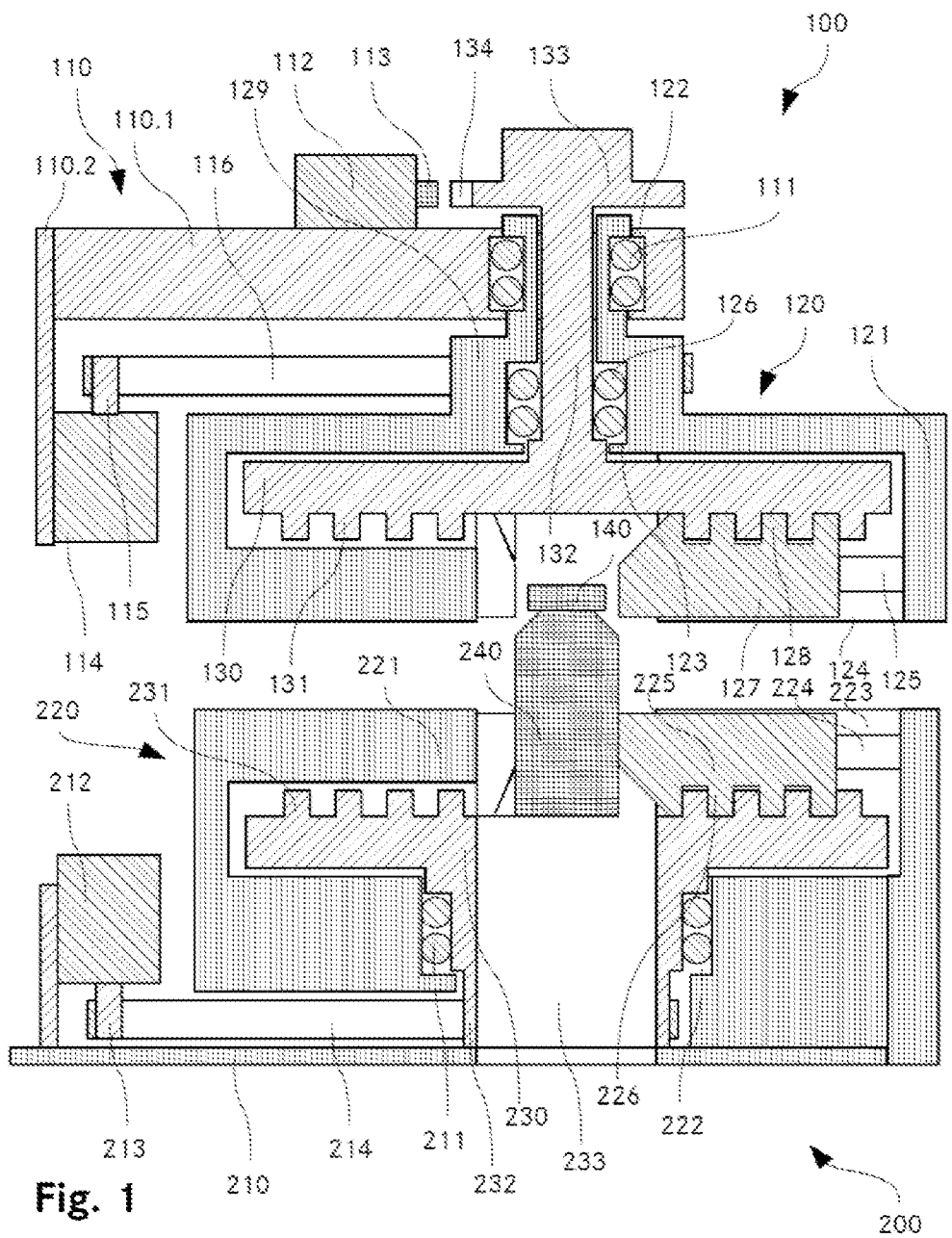
FIG. 1 shows a schematic sectional illustration of the first and the second holding device.

FIG. 1 shows a schematic sectional illustration of the first holding device 100 and the second holding device 200. The second, lower holding device 200 serves for holding the container 240, and the first, upper holding device 100 serves for holding the screw cap 140. In the method for opening a screw cap 140 of a container 240, the container 240 is inserted into and held in the second holding device 200. The first holding device 100 is then positioned in such a manner that the screw cap 140 can be grasped by the first holding device 100. After the grasping, the first holding device is then rotated about the axis of rotation thereof in the opening direction, in particular anticlockwise, and therefore the screw cap 140 is unscrewed from the container 240. In order to screw down a container 240 with a screw cap 140, a container 240, with a screw cap 140 loosely placed thereon, is correspondingly inserted into the second holding device 200 and fixed, whereupon the screw cap 140 is grasped by the first holding device 100 and rotated counter to the opening direction or in the closing direction, in particular in the clockwise direction. The first holding device 100 and the second holding device 200 are described in detail below with respect to FIG. 1.

The first holding device 100 substantially comprises a holder 110, via which the holding device 100 is mounted on a linear guide (see below) and on which the first jaw chuck 120 is rotatably mounted.

The holding device 100 comprises a strip 110.1, on which, at the one end via a ball bearing 111, the first jaw chuck 120 is mounted rotatably about an axis oriented at right angles to the strip 110.1. In addition, the changeover switch 112 with the magnetically activatable bolt 113 is mounted on the strip 110.1. A mounting plate 110.2, to which the driving motor 114 is fastened, with the drive shaft 115 parallel to the mounting plate 110.2 and at right angles to the strip 110.1, is mounted at the second end of the strip 110.1 and at right angles thereto. The driving motor 114 and the changeover switch 112 are arranged on opposite sides of the strip 110.1.

The first jaw chuck 120 substantially comprises a jaw chuck housing 121 and a threaded plate 130, which is mounted rotatably within the jaw chuck housing 121 and has a drive shaft 132.

The jaw chuck housing 121 of the first jaw chuck 120 has an internally hollow, circular-cylindrical basic shape with a bearing cylinder 129 arranged coaxially with respect to the circular cylinder. The threaded plate 130 which is in the shape of a circular disk is mounted in the circular-cylindrical basic shape. The bearing cylinder 129 comprises two substantially circular-cylindrical regions. The first region of the bearing cylinder 129, which region directly adjoins the basic shape, comprises, along the inner walls, an encircling groove in which a ball bearing 126 for the drive shaft 132 of the threaded plate 130 is arranged. The second region of the bearing cylinder 129, which region adjoins the first region, comprises, on the outer side, an encircling groove, in which a ball bearing 111 is arranged. The jaw chuck housing 121 is mounted rotatably on the holder 110 via the ball bearing 111. The ball bearing 126 and the ball bearing 111 are both arranged coaxially with respect to the axis of rotation of the jaw chuck housing 121 or coaxially with respect to the individual cylinder axes of the first region, the second region and the circular-cylindrical basic shape.

On the side opposite the cylindrical regions, the jaw chuck housing 121 has an opening for receiving a screw cap 140. The opening is oriented coaxially with respect to the ball bearing 126 or with respect to the circular-cylindrical basic shape of the jaw chuck housing 121. Three radially oriented slots 124 (only one slot 124 is apparent in FIG. 1), in which the jaws 127 of the first jaw chuck 120 are radially guided, open into said opening. The three slots 124 are arranged in a star-shaped and regular manner, that is to say, with an intermediate angle in each case of 120° (see below, with respect to FIG. 2). The slots 124 are in each case provided on both sides with grooves 125 for the radial guidance of the jaws 127, and therefore an axial movement of the jaws 127 can be prevented. For this purpose, the jaws 127 comprise lateral guide strips which are guided radially in the form of a sliding guide in the grooves 125. The jaws 127 can therefore be moved to and fro in the radial direction. In order to hold a screw cap 140, the jaws 127 are guided radially inward.

The threaded plate 130 is in the form of a circular disk. On one side, the threaded plate 130 is provided with a helical thread 131. The threaded plate 130 is mounted rotatably in the jaw chuck housing 121 in the cavity of the circular-cylindrical basic body. For this purpose, on that side of the threaded plate 130 which is opposite the helical thread 131, said threaded plate is connected coaxially with respect to the circular disk to a drive shaft 132. The drive shaft 132 is mounted rotatably in the bearing cylinder 129 via the ball bearing 126. Said drive shaft 132, at the end thereof opposite the threaded plate 130, is connected to a blocking wheel 133. Said likewise circular-cylindrical blocking wheel 133 projects out of the bearing cylinder 129 and comprises, on the outer side, a recess 134 in which the bolt 113 of the magnetic changeover switch 112 engages, and therefore a rotation of the threaded plate 130 can be blocked. In a corresponding manner, the magnetic changeover switch 112 is mounted on strip 110.1 in such a manner that, by activation of the changeover switch 112, engagement of the bolt 113 in the recess 134 can be achieved. In the present case, the changeover switch 112 is designed in such a manner that, in the energy-free state, the bolt 113 does not engage in the recess 134. However, it is clear that the changeover switch 112 can also be designed in such a manner that, in the energy-free state, the bolt 113 engages in the recess 134.

While the second region of the bearing cylinder 129 is mounted rotatably in the strip 110.1 via the ball bearing 111, the outer region of the first region of the bearing cylinder 129 is designed as a drive wheel or rolling surface for a drive belt 116 which is driven by the drive motor 114. For this purpose, said outer region can be appropriately structured or can comprise other known guide aids for the drive belt 116.

The jaws 127 are movable radially via the helical thread 131 of the threaded plate. The jaws 127 have a rectangular basic shape in a plane at right angles to the cylinder axis of the jaw chuck housing 121. That surface of the jaws 127 which projects in the axial direction into the cavity of the jaw chuck housing 121 is provided with tangential grooves which form a thread 128 which acts as a counterpart to the helical thread 131 of the threaded plate 130. The jaws 127 are in each case in engagement by means of the thread 128 thereof with the helical thread 131 of the threaded plate 130. If the threaded plate 130 is then rotated relative to the jaw chuck housing 121, the jaws 127, depending on the direction of rotation, are moved radially in the direction of the axis of rotation or radially counter to the direction of the axis of rotation. Owing to the thread pitch of the helical thread 131 or of the thread 128 of the jaws, said jaw chuck 120 is what is referred to as a self-locking three jaw chuck. The term self-locking is understood as meaning that the positions of the jaws 127 in the jaw chuck 120 cannot change independently, for example due to shaking or due to too low a degree of friction. Of course, the self-locking can also be influenced by other factors, such as the lubrication, surface structure, etc., in addition to the thread pitch.

For the first jaw chuck 120, there are therefore two operating modes which can be selected by the changeover switch 112.

In the first operating mode, the changeover switch 112 is energy-free, and therefore the bolt 113 does not engage in the recess 134 of the blocking wheel 133. If the drive motor 114 is then activated, the rotational movement of the drive shaft 115 is transmitted by means of drive belt 116 to the first region of the bearing cylinder 129 and therefore sets the jaw chuck housing 121 into a rotational movement. Since the first jaw chuck 120 is self-locking and the blocking wheel 133 is not blocked by the bolt 113, the threaded plate 130 rotates together with the jaw chuck housing 121. The first jaw chuck 120 is therefore rotated in its entirety without the jaw chuck 120 of the jaws 127 being activated. In this state, a screw cap 140 which is already held by the first jaw chuck is rotated.

In the second operating mode, the changeover switch 112 is activated such that the bolt 113 engages in the recess 134 of the blocking wheel 133. If the drive motor 114 is then activated, the rotational movement of the drive shaft 115 is transmitted in turn by means of drive belt 116 to the first region of the bearing cylinder 129 and therefore sets the jaw chuck housing 121 into a rotational movement. Since the blocking wheel 133 is then blocked by the bolt 113, the threaded plate 130 does not rotate together with the jaw chuck housing 121. The first jaw chuck 120 is therefore rotated in its entirety while the threaded plate 130 is fixed. By means of this relative rotation, the jaws 127 of the jaw chuck 120 are moved radially inwards or outwards depending on the direction of rotation. In this operating mode, a screw cap 140 can be grasped or released.

In order to be able to loosen or tighten a screw cap 140 from or on a container 240 with a rotational movement of the first jaw chuck 120, the container 240 has to be able to be held with respect to the first holding device 100. For this purpose, the device preferably comprises a second holding device 200 with a second jaw chuck 220 which is arranged below the first jaw chuck 120.

In the present case, the second jaw chuck 220 only takes on the function of holding the container 240.

The second jaw chuck 220 comprises a jaw chuck housing 221 which is mounted fixedly on a mounting plate 210. The jaw chuck housing 221 substantially has a circular-cylindrical basic shape with a cavity for a circular ring plate 230.

One surface of the circular ring plate 230 is provided with a helical thread 231 which, in turn, can move the jaws 225 of the second jaw chuck 220—this takes place analogously to the first jaw chuck 120. For the description of the function of the jaws 225, the thread 226 of the jaw with the helical thread 231 of the circular ring plate 230, the radial slots 223 and the grooves 224 for guiding the jaws, reference is made to the description of the first jaw chuck 120. On that side of the circular ring plate 230 which is opposite the helical thread 231, a drive shaft 232, substantially in the form of a hollow cylinder, is connected to the circular ring plate 230. A ball bearing 211 is arranged revolving around the drive shaft 232 in such a manner that the circular ring plate 230 is rotatable on the jaw chuck housing 221. In the present embodiment, the jaw chuck housing 221 and the drive shaft have complementary steps between which the ball bearing 211 is held.

The inside diameter of the drive shaft 232 corresponds to a central opening in the circular ring plate 230, in the second jaw chuck housing 221, and to an opening in the mounting plate 210. All of the openings are arranged coaxially in such a manner that, when the jaw chuck is open, there is a continuous opening in the second jaw chuck 220. Container and screw cap can therefore optionally drop through the continuous opening, in particular if the container is identified as a reject. On the other hand, after activation of the screw cap, the containers can also be removed from below, through the continuous opening. In principle, there is therefore the possibility of loading or unloading the second jaw chuck from above and from below.

A driving motor 212 for the second jaw chuck 220, which driving motor can drive a drive belt 214 via a drive shaft 213, is mounted on the mounting plate 210. For this purpose, the drive shaft 232 has a running surface for the drive belt 214, which running surface is arranged opposite the circular ring plate 230 with respect to the ball bearing 211. The jaw chuck housing 221 has a channel adjacent to the mounting plate 210 for guiding the drive belt 214.

When the drive 212 is actuated, the jaws 225 are moved radially inward or outwards, depending on the direction of rotation, and therefore a container 240 can be correspondingly held or released.

Figure 2:
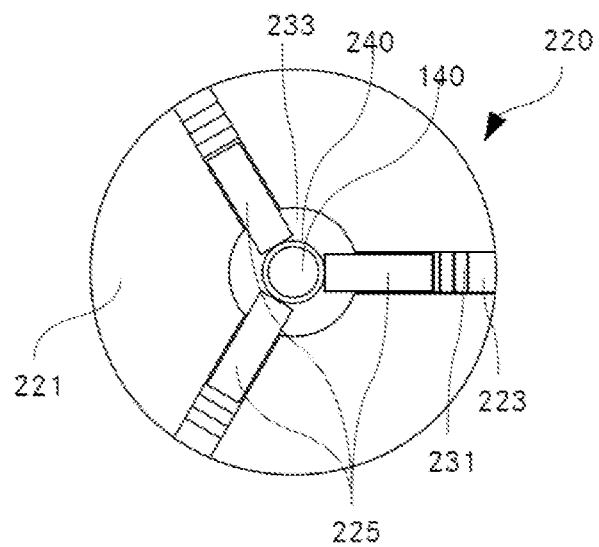
FIG. 2 shows a schematic illustration of a top view of the three jaw chuck of the second holding device.

FIG. 2 shows a schematic illustration of a top view of the second three jaw chuck 220 of the second holding device 200. It is apparent here that the jaw chuck housing 221 is of substantially circular-cylindrical design and, for the guiding of the jaws 225, comprises three slots 223 arranged in a star-shaped manner. The container 240 (with the screw cap 140) can drop through the central opening 233. Finally, the circular ring plate 230 with the helical thread 231 is apparent in each case in the slots 223. In the state illustrated, a container 240 is held by the jaws 225.

In particular if containers 240 are intended to be inserted directly from above into the second jaw chuck 220 or directly from below into the first jaw chuck 120, at least one of the two holding devices 100, 200 is then preferably movable to and fro in at least one direction. "Directly" is understood as meaning here that the container 240 does not pass the other jaw chuck beforehand.

Figure 3:
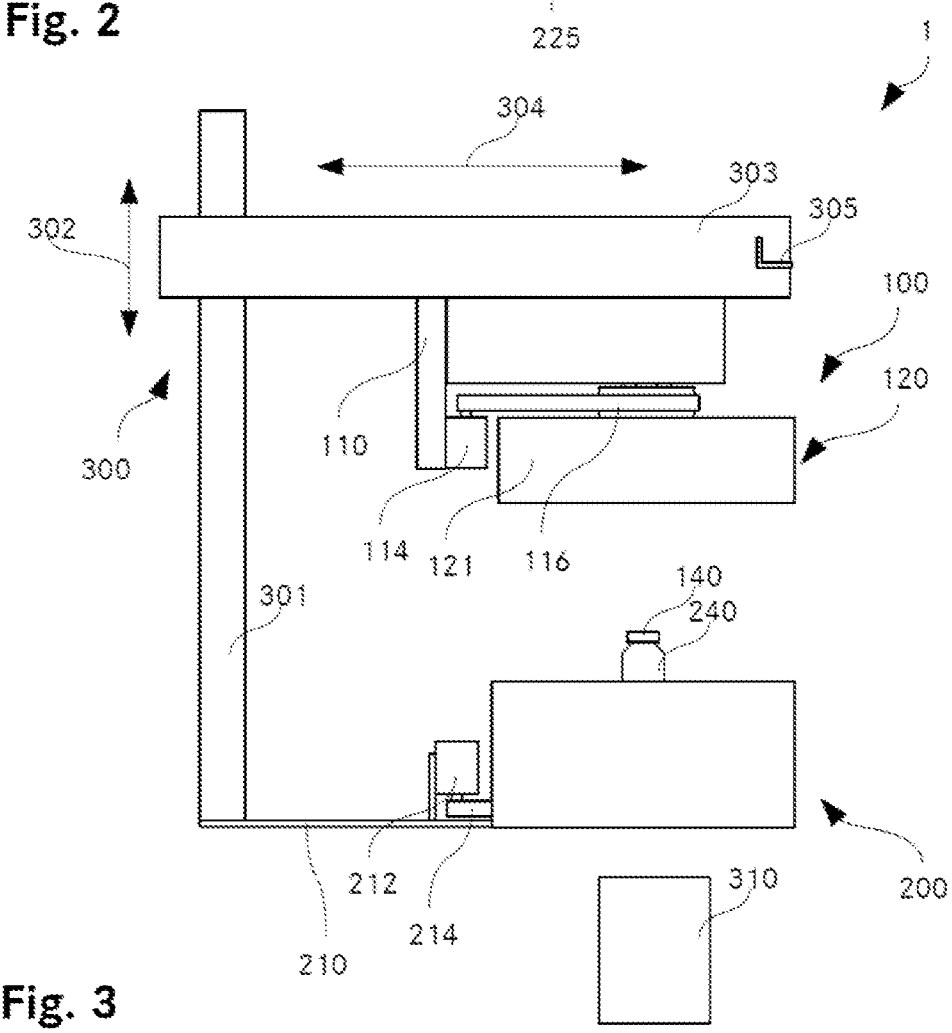
FIG. 3 shows a schematic illustration of the device for activating a rotary closure, wherein the first holding device is movable in a plane via a y,z guide.

FIG. 3 shows a schematic illustration of the device for activating a rotary closure 1, wherein the first holding device 100 is movable in a vertical plane by a y,z guide 300. The two holding devices 100, 200 correspond to those of FIG. 1, and therefore reference is made to the above description for the details.

In the present embodiment, the first holding device 100 is fastened to a y rail which is movable on a z rail 303 in the y direction 304 and in the z direction 302. The y,z guide 300 is not motorized, that is to say, it is drive-free in the present case. In the present embodiment, the first holding device 100 is moved by an external drive (see below). For this purpose, the z rail 303 comprises an L-shaped slot 305 in which a corresponding, L-shaped element (see below) of a robot can engage in a positive-locking manner and can therefore move the first holding device 100 in the y,z plane.

In the illustration according to FIG. 3, a container 240 together with screw cap 140 is already inserted in the second holding device 200. The first holding device 100 is correctly positioned with respect to the y direction 304, and therefore said holding device can then be moved downwards in the z direction 302 in order, by means of the first jaw chuck 120, to grasp the cap 140 (second operating mode, bolt of the changeover switch is activated, and therefore the threaded plate 130 rotated together with the jaw chuck housing 121) and subsequently to rotate said cap, for opening or closing purposes (first operating mode, bolt of the changeover switch is not activated).

Following the activation of the screw cap 140, the first jaw chuck 120 is released again. In order to be able to remove the container 240 out of the second holding device from above, the y rail is now moved together with the first holding device 100 upwards in the z direction 302 and then in the y direction 304. The space above the container 240 therefore becomes free for the access of a robot or the like. After the container 240 has been grasped, the second jaw chuck 220 is released.

Alternatively, however, the two jaw chucks 120 can also be released, and therefore the container 240 can drop through the continuous opening into a catching container 310.

As already mentioned, the y,z guide itself is of drive-free design. When a screw cap 140 is activated by the first holding device 100, the holding device 100 is moved in a drive-free manner in the z direction by the thread pitch of the screw cap 140. This has the advantage that no adjustment is necessary if the thread pitch changes. For the moving of the first holding device, an external robot, preferably a robot which can already take on functions, such as container transport or removal of samples, is therefore provided. The efficiency of the robot is therefore optimized, but also the costs for the device and the maintenance are reduced.

Figure 4:
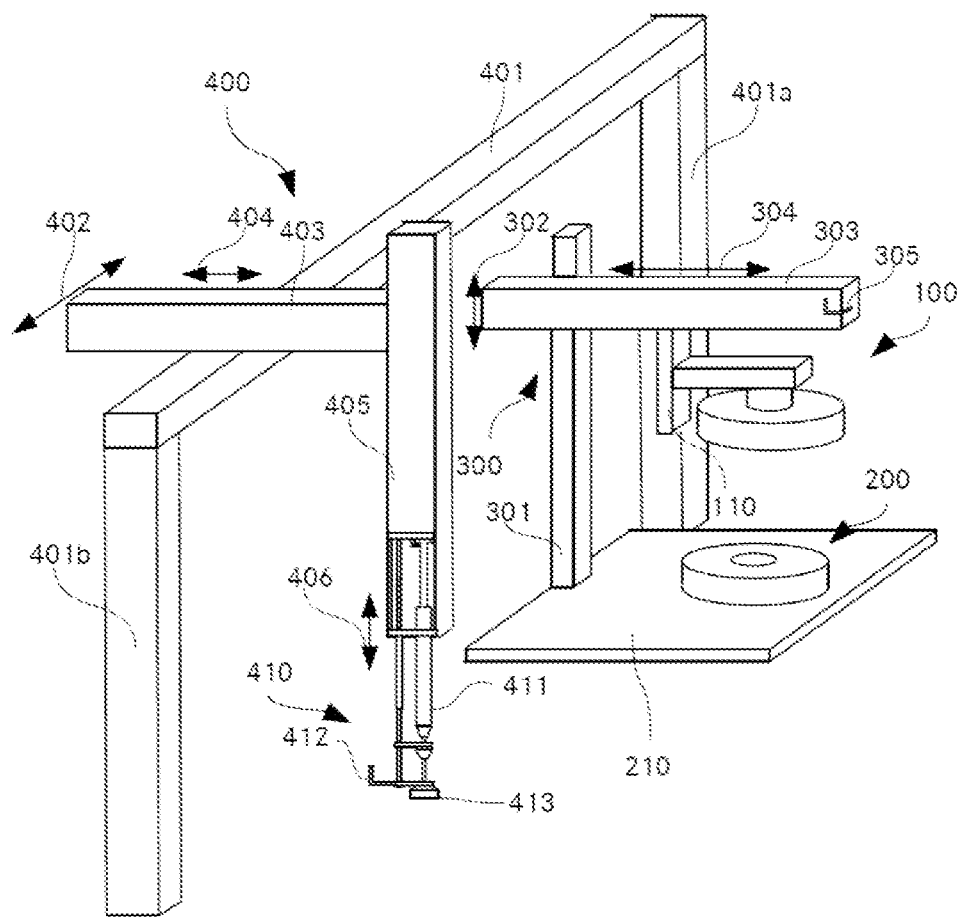
FIG. 4 shows a schematic oblique view of an arrangement comprising a device according to FIG. 3 and an x,y,z robot for moving the first holding device.

FIG. 4 illustrates a schematic oblique view of an arrangement comprising a device 1 according to FIG. 3 and an external x,y,z robot 400 for moving the first holding device 100. In the present case, the x,y,z robot 400 is designed in such a manner that both the y,z guide 300 can be operated and container 240 can be transported or samples can be removed from a container. The last (one or two) functions can also be dispensed with, or they can be replaced by one or more other functions (SPME device, stirring device, heating element, gripping arm, etc.). The functions are in each case adapted to the field of use.

In the present case, the x,y,z robot 400 comprises an x rail 401, a y rail 403 and a z rail 405. The x rail 401 comprises two supports 401a, 401b, via which the x,y,z robot 400 is mounted on a rest. A y rail 403 is held on the x rail 401 so as to be movable in the x direction 402 and in the y direction 404. Finally, the z rail 405, on which, in the present case, a syringe unit 410 is held so as to be movable in the z direction 406, is held on the y rail 403.

The syringe unit 410 comprises a syringe 411 for removing samples, for example from a container with a septum or the like. The syringe unit 410 furthermore comprises a holding device 413 for grasping a container 240. In the present case, the holding device 413 is designed as a magnetic cap, but can also comprise a gripper or the like.

Finally, the syringe unit 410 comprises an L-shaped element 412 which can engage in the L-shaped slot 305 of the y rail of the y,z guide in order to move the first holding device in the y,z plane via the y,z guide.

Figure 5:
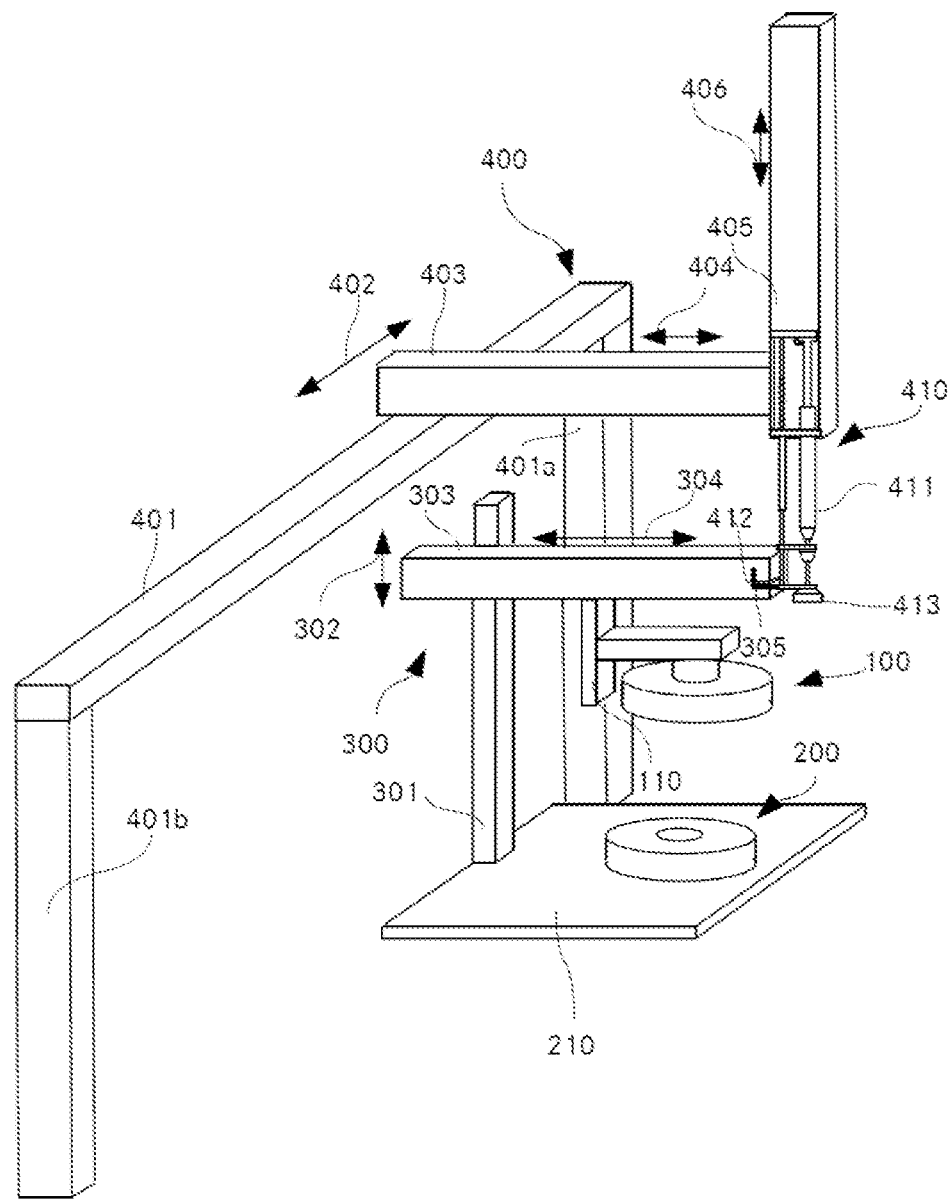
FIG. 5 shows a schematic oblique view of the arrangement according to FIG. 4, wherein the x,y,z robot is in engagement with the y,z guide.

FIG. 5 shows a schematic oblique view of the arrangement according to FIG. 4, wherein the x,y,z robot 400 is in engagement with the y,z guide 300. For this purpose, the x,y,z robot 400 has been positioned in the y,z plane in such a manner that the L-shaped element 412 is oriented in the x direction 402 in alignment with the L-shaped slot 305 of the y rail. The x,y,z robot 400 is then moved with the y rail 403 in the x direction 402 until the L-shaped element 412 is in engagement with the L-shaped slot 305. It should be noted here that, in the present embodiment, the y rail 303 of the y,z guide 300 is not movable in the x direction 402, and therefore secure grasping by the L-shaped element 412 is ensured. In this configuration according to FIG. 5, the first holding device 100 can then be moved in the x,y plane by means of the x,y,z robot 400.

The jaw chuck 120 or 220 does not absolutely have to be designed as a three jaw chuck. In a further embodiment, only two or more than three, in particular four jaws 127 can also be provided.

In a further embodiment, the threaded plate 130 can comprise a central opening, and the drive shaft 132 together with the blocking wheel 133 can be designed as a hollow body, that is to say, substantially as a cylinder jacket. Therefore, for example, screw caps 140 can be introduced into the first jaw chuck 120 from above, and therefore screwing down of containers 240 with screw caps 140 can be achieved more efficiently. Containers 240, with or without screw caps 140, can also be introduced from above into the device 1, and therefore the latter can be of more compact design, in particular since access between the two jaw chucks 120, 220 does not necessarily have to be achievable. The container 240 could also be introduced from below through the central opening 233 in the second jaw chuck 220 and the cap 140 could also be introduced, as described above, from above. Finally, the second jaw chuck 220 can also be guided and lowered by a container 220, and therefore the containers 220 can be kept ready, for example, on a conveyor belt or the like. Robot transport of the containers 220 can therefore be dispensed with.

Figure 6:
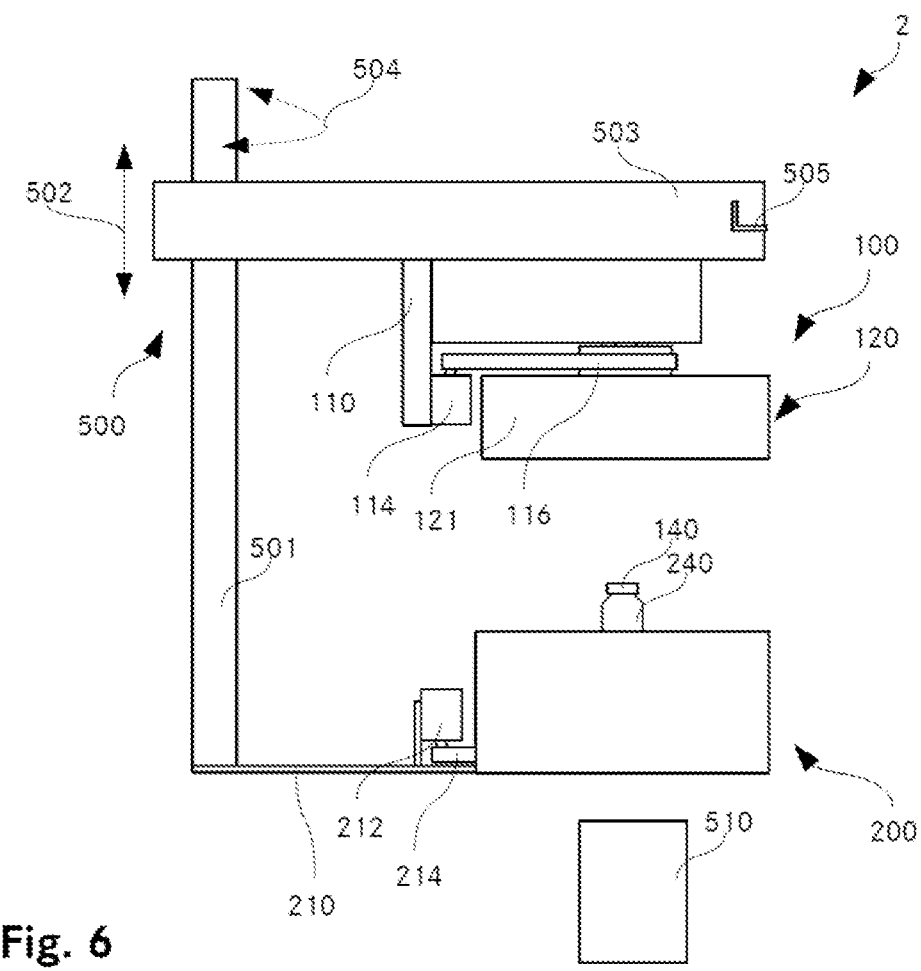
FIG. 6 shows a schematic illustration of a further embodiment of a device for activating a rotary closure, wherein the first holding device is movable via along a region of a cylinder jacket.

FIG. 6 shows a schematic illustration of a further embodiment of a device 2 for activating a screw cap 140, wherein the first holding device 100 is movable via along a region of a cylinder jacket. The device 2 substantially corresponds to the device 1, wherein, instead of numbers in the 300s, numbers in the 500s are in each case used. Only the differences are discussed below. The cylinder coordinate system is by a z rail 501 which is arranged vertically, and also a y arm 503, which is movable in the z direction 502 on the z rail 501 and, in addition, is rotatable about the z rail 501 in the direction of rotation 504. An L-shaped slot 505 for the x,y,z robot 400 is provided in turn at the distal end of the y arm 503. The L-shaped slot 505 here is preferably not oriented precisely in the direction of rotation 504 of the y arm 503, and therefore, during each movement, a positive-locking connection of the L-shaped slot 505 and of the L-shaped element 412 remains ensured.

In variants, for this embodiment, instead of the L-shaped slot 505, it is therefore also possible just to provide a bore, which is oriented in the z direction, from below at the distal end of the y arm 503. In this case, the x,y,z robot 400 would have a corresponding pin which can enter the bore. This design is of advantage since, during the pivoting operation by the x,y,z robot 400, the pivoting movement of the y arm 503 itself would not necessarily have to be taken into consideration.

In principle, the two jaw chucks 120, 220 can also be interchanged, with the effect that the lower jaw chuck 220 is of rotatable and activatable design while the upper jaw chuck 120 is merely activatable. That is to say, in principle the screw cap 140 can also be held while the container 240 is rotated. Instead of an external x,y,z robot, the y,z guide can also be motorized.

The driving motors 114 and 212 are preferably torque-controlled motors, and therefore a compressive force on the container 240 or on the screw cap 140 can be adapted in such a manner that damage can be avoided.

In summary, it can be stated that, according to the invention, a device for activating screw closures is provided, which device can be produced particularly cost-effectively and can be integrated in a simple manner in existing systems. In addition, the device according to the invention is distinguished by improved efficiency of individual mechanical elements. In particular, existing resources can be optimally used, and therefore the device can be constructed more simply and can be formed in particular with fewer dedicated drive units.

LIST OF REFERENCE NUMBERS (NOT FILED)

1,2 Device for activating a rotary closure
100 First holding device
110 Holder
110.1 Strip
110.2 Mounting plate
111 Ball bearing
112 Magnetic changeover switch
113 Bolt
114 Driving motor
115 Drive shaft
116 Drive belt
120 First jaw chuck
121 Jaw chuck housing
122 Outer groove
123 Inner groove
124 Radial slot
125 Groove
126 Ball bearing
127 Jaw
128 Thread
129 Bearing cylinder
130 Threaded plate
131 Helical thread
132 Drive shaft
133 Blocking wheel
134 Recess
140 Screw cap
200 Second holding device
210 Mounting plate
211 Ball bearing
212 Driving motor
213 Drive shaft
214 Drive belt
220 Second jaw chuck
221 Jaw chuck housing
222 Inner groove
223 Radial slot
224 Groove
225 Jaw
226 Thread 230 Circular ring plate
231 Helical thread
232 Drive shaft
233 Central opening
240 Container
300 y,z guide
301 z rail
302 z direction
303 y rail
304 y direction
305 L-shaped slot
310 Catching container
400 External x,y,z robot
401 x rail
401a, 401b Supports
402 x direction
403 y rail
404 y direction
405 z rail
406 z direction
410 Syringe unit
411 Syringe
412 L-shaped element
413 Magnetic picking-up device
500 y,z guide
501 z rail
502 z direction
503 y arm
504 Direction of rotation
505 L-shaped slot
510 Catching container

The invention claimed is:

1. A device for screwing and/or unscrewing a screw cap of a container comprising a first holding device for holding the screw cap, said first holding device including a first jaw chuck mounted in a jaw chuck housing, said jaw chuck housing being mounted rotatably on a holder;

a threaded plate mounted rotatably within said jaw chuck housing, said threaded plate having a drive shaft;

a drive motor which is coupled to said jaw chuck housing to set said jaw chuck housing into rotational movement; and jaws arranged in engagement with the threaded plate, such that when said jaw chuck housing is set into said rotational movement relative to said threaded plate, said jaws are moved radially in the direction of or counter to the direction of an axis of rotation of said threaded plate in order to grasp or to release a screw cap, wherein said first holding device comprises a changeover switch configured to be switched between a first operating mode and a second operating mode, wherein, when the changeover switch is switched to the first operating mode, said rotational movement of said jaw chuck housing together with a rotation of said threaded plate is allowed, and wherein, when the changeover switch is switched to the second operating mode, said rotation of the threaded plate is blocked such that said jaw chuck housing is rotated by said rotational movement relative to said threaded plate.

2. The device according to claim 1, wherein said threaded plate comprises a blocking wheel connected to the drive shaft, said blocking wheel including a recess on an outer side into which a bolt of the changeover switch engages in order to block the rotation of the threaded plate.

3. The device according to claim 1, wherein said changeover switch comprises a magnetically activated bolt.

4. The device according to claim 2, wherein said bolt is magnetically activated and does not engage said recess in an energy-free state.

* * * * *